United States Patent [19]

Burchall et al.

[11] Patent Number: 4,795,639

[45] Date of Patent: Jan. 3, 1989

[54] POTENTIATING FORMULATIONS

[75] Inventors: James J. Burchall; Stanley R. M. Bushby, both of Research Triangle Park, N.C.; Robert Cullen, Langton; Michael J. W. Dunkley, Crowborough, both of England; Robert Ferone, Research Triangle Park, N.C.

[73] Assignee: Burroughs Wellcome Co., Research Triangle Park, N.C.

[21] Appl. No.: 778,264

[22] Filed: Mar. 16, 1977

Related U.S. Application Data

[63] Continuation of Ser. No. 277,885, Aug. 4, 1972, abandoned.

[30] Foreign Application Priority Data

Aug. 5, 1971 [GB] United Kingdom ............... 71/36774

[51] Int. Cl.⁴ .................. A61K 31/505; A61K 31/63; A61K 31/625

[52] U.S. Cl. .................................... 514/249; 514/258

[58] Field of Search ............................... 424/251, 254

[56] References Cited

U.S. PATENT DOCUMENTS

| | | | |
|---|---|---|---|
| 2,909,522 | 10/1959 | Hitchings et al. | 424/251 |
| 3,635,978 | 1/1972 | Wood et al. | 260/256.4 C |

Primary Examiner—Jerome D. Goldberg
Attorney, Agent, or Firm—Donald Brown

[57] ABSTRACT

A composition for testing or treating microbial systems or infections, comprising an effective potentiating amount of a microbial dihydropteridine antagonist, which itself inhibits hydroxymethyldihydropteridine pyrophospokinase and has a sufficiently low toxicity, in combination with an effective amount of a competitor of para-aminobenzoic acid or an inhibitor of dihydrofolate reductase or both, its method of preparation, and its use in the inhibition of the production of dihydrofolic acid by microorganisms under in vivo or in vitro conditions.

4 Claims, No Drawings

POTENTIATING FORMULATIONS

This is a continuation of application Ser. No. 277885, filed Aug. 4, 1972, now abandoned.

This invention relates to compositions useful in the treatment of microbial infections in mammals and poultry.

Tetrahydrofolate co-factors are essential metabolites in all cells for the biosynthesis of purines, thymidylic acid, serine and several other biologically important compounds. Most of these co-factors are one-carbon adducts of tetrahydrofolic acid. The ultimate source of these for higher animals and man is food, containing preformed folates usually in the form of vitamins.

In microorganisms, the co-factors are synthesised from simpler chemicals. Generally the bio-synthetic process first provides 'dihydropteridine' (Pt), i.e., 2-amino-4-hydroxy-6-hydroxymethyl-7,8-dihydropteridine (HMPt) pyrophosphate ester, from its immediate precursor HMPt in the presence of the enzyme hydroxymethyldihydropteridine pyrophosphokinase (HMPPS). Pt is then condensed with p-aminobenzoic acid(pAB) in the presence of the enzyme dihydropteroatesynthetase to form dihydropteroic acid (DPtA). This intermediate is further condensed with a glutamate to form dihydrofolic acid (DFA or 'folate') which is then enzymatically reduced to provide the essential tetrahydrofolate, for instance in bacteria and other microorganisms.

The provision of the 'folate' from the basic building blocks, i.e. pteridine, pAB, and glutamate, and the further conversion of this into the tetrahydrofolate is known to be inhibited in two different ways. For instance sulphonamides displace pAB in the above reaction scheme. Because of their close structural resemblance to pAB, sulphonamides or similar other 'competitors' enter the biosynthesis and prevent the formation of DPtA, and of DFA, and are therefore antimetabolites for the metabolite pAB.

It is also known that compounds which are 'inhibitors' of the enzyme dihydrofolic acid reductase block the synthetic step leading to tetrahydrofolate. A considerable number of pyrimidine derivatives show substantial anti-microbial properties on the basis of such blockage.

It was also established later that such inhibitors may act synergistically with sulphonamides, i.e. there can be a sequential double blockade and a strong mutual potentiation of the antibacterial effects of the two materials. The range of antimicrobial action exerted by such combinations is considerably wider than that expected from the activity of either drug, and organisms which are only marginally sensitive to the individual agents become very sensitive to the combinations.

It was also suggested hypothetically that antimetabolites to Pt could inhibit the biosynthesis of DPtA (and DFA) (cf. Hitchings and Burchall *Advances in Enzymology*, 27, 417-468 (1965)) but compounds so far tested for the purpose have been disappointing, being either inactive or too toxic or sometimes both (cf. the compounds described in British Pat. Nos. 981,506 and 987,916). It has been established that, for antimicrobial purposes, it is a prerequisite for the effective antagonism of Pt that the compound should be an inhibitor of HMPPS without also acting as an antimetabolite to the dihydropteridine that serves as a cofactor for the hydroxylation of phenylalanine and tyrosine, precursors of the catecholamines, such as norepinephrine, that have important actions as regulators of cardiovascular systems. Such an antimetabolic effect could lead to prohibitive toxicity to avian or mammalian species, which are normally the hosts infected with the microbes.

Furthermore it has been discovered that substances which fulfil the requirements, i.e. inhibition of HMPPS combined with low toxicity to host species, as demonstrated for instance in chicks and rats, not only inhibit the growth of micro-organisms to some extent but unexpectedly act with most remarkable synergistic effect when combined with a competitor of pAB, e.g. sulphonamides and similar compounds, or with selective inhibitors of dihydrofolate reductase, or with a combination of both of these types of anti-microbial agents.

In one aspect therefore there is provided a composition for testing microbial systems or infections, comprising an effective potentiating amount of a microbial dihydropteridine antagonist, hereinafter called a 'potentiator', which itself inhibits HMPPS and has a sufficiently low toxicity, in combination with an effective amount of a competitor or inhibitor, or both, as hereinbefore defined.

The microbial infections against which the combinations of this invention are effective are protozoal or bacterial infections caused by those microorganisms which synthesise at least a substantial part of their tetrahydrofolate co-factor requirements. More specifically these infecting microorganisms are those which adequately absorb the pharmaceutical combinations disclosed herein and further are those in which these combinations have a synergistic effect in interfering with the de novo synthesis of the required tetrahydrofolate co-factors.

It has been found specifically that, when potentiators are combined with an amount of the competitor and/or the inhibitor which is not ordinarily sufficient to be effective as an antimicrobial agent in its own right, the combination of a potentiator with this normally ineffective amount of the competitor and/or the inhibitor provides a composition which in totality acts an an effective antimicrobial agent. This is especially notable when the amount of the potentiator is so low that it has substantially no microbial effeet at the particular level, yet in the combination the potentiation is marked, in some instances very marked.

In accordance with the above therefore, the term "an effective amount" used in conjunction with the terms a dihydrofolic reductase 'inhibitor' and a para-aminobenzoic acid 'competitor' means either (a) an amount of the 'inhibitor' or 'competitor' which is effective to a degree as an antimicrobial agent in its own right but which is potentiated by the use of a potentiator or (b) an amount of the 'inhibitor' or 'competitor' which is ineffective as an antimicrobial agent but which when combined with a potentiator provides a composition which is an effective antimicrobial agent. An "effective potentiating amount" means an amount of the potentiator which increases the activity of an inhibitor and/or a competitor so as to provide an improved or adequate effectiveness for the whole combination.

It should be emphasised that the inhibition of the biosynthetic processes by such means could be termed as competitive antagonism in all three instances, and there might be potentiation between all three types of agents. The terms 'inhibitor', 'competitor', and 'potentiator' are arbitrary and should only serve as convenient names for the appropriate type of components in combination products described and claimed in the present specification The inhibiting activity against HMPPS of a selected potentiator can, for instance, be tested by monitoring the transfer of the terminal phosphate ATP-γ-$P^{32}$ to dihydropteridine. It was found that the concentrations required for 50% inhibition of the formulation of Pt ($IC_{50}$) in such tests are well correlated and within the margin of error obtained by other relevant tests in this respect, which measure the inhibition of either of the two enzymes involved in the formation of HMPt and DPtA. Such inhibition may for instance, be easily and simply carried out by incubating an extract of E. coli with pAB-7-$C^{14}$, ATP, Mg and dihydropteridine. The formation of the dihydropteroate-$C^{14}$ can be quantitatively assayed after separating the unreated pAB substrate, for instance by chromatography. It has been found that compounds possessing in such tests an $IC_{50}$ value of about 100 μM or less, usually below 50 μM represent compounds exerting a useful potentiating effect, provided their toxicity in the appropriate vertebrates is acceptable. Preferably the value is 25 μM or less, such as in the range between 2 to 12 μM. Generally a value below 7 μM is desirable.

As explained above, with the present invention it is essential that the potentiator should not have a prohibitive toxicity to the mammalian or avian hosts' cardiovascular systems. While low toxicity is therefore an essential requirement, a therapeutic index incorporates both the activity and toxicity required by the present invention and could be used with advantage for the selection of potentiators.

The therapeutic index is defined as the ratio of the maximum tolerated dose to the minimum effective dose and in most cases is preferably greater than 10, suitably at least 5 and in exceptional circumstances at least about 3 for humans possibly as low as 2 for humans.

In particular, compounds which show structural similarities to Pt, i.e. various pteridines having the required inhibitory and toxicity properties can be selected with advantage for the purposes of the present invention. For instance 2-amino-4-hydroxy-7,8-dihydropteridines substituted on the 6-position through a carbon atom and bisubstituted at the seventh position are particularly promising in showing potentiating effects.

It has now been found in particular that pteridines of formula (I)

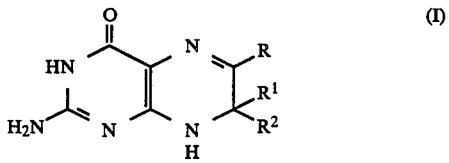

or tautomeric forms thereof, wherein R is an alkyl group, optionally substituted with a hydroxy group, with one or more halogen atoms or with an optionally substituted phenoxy group, and $R^1$ and $R^2$ are the same or different and each is an alkyl group, or $R^1$ and $R^2$ together form a spirocycloalkyl ring system having 4 to 6 carbon atoms outside the pteridine ring structure, or pharmaceutically acceptable salts thereof (all of which are hereinafter to be included within the scope of the compounds of formula (I)), are effective as potentiators, as hereinbefore defined.

In the compounds of formula (I) the alkyl groups of substituents R, $R^1$ and $R^2$ have from 1 to 4 carbon atoms. The phenoxy group may be substituted with one or more alkoxy, amino, alkyl or hydroxy groups or halogen atoms, in particular in the para position. The halogen atoms may be fluorine, chlorine, bromine or iodine, and preferably appear as a mono- or di-substituent. The bromo-substitution is especially convenient to prepare.

A particular group within the scope of formula (I) is represented by compounds wherein R is limited to a 6-alkyl or 6-hydroxyalkyl group. In these compounds the substituents $R^1$ and $R^2$ are as defined with reference to formula (I), but it is preferred that they are either methyl or ethyl groups. For instance the compounds 2-amino-4-hydroxy-6-hydroxymethyl-7,7-dimethyl-7,8-dihydropteridine, hereinafter referred to as DMHP, and 2-amino-4-hydroxy-6-hydroxymethyl-7,7-diethyl-7,8-dihydropteridine have been found to have outstanding potentiating properties. These compounds and their analogues have been described in the specification of U.K. patent application Nos. 3301/70, U.S. Pat. No. 3,635,978, and further methods for making them have been discussed in an article by Pfleiderer and Zondler in Chem. Ber. 99, 3008 (1966) and in the specification of U.K. patent application No. 36289/70, Belgian Pat. No. 770,577.

Another group within the scope of formula (I) is represented by compounds wherein R is limited to a phenoxyalkyl group, in particular a phenoxymethyl group, but the phenoxy group may also be substituted as hereinbefore mentioned. The $R^1$ and $R^2$ substituents are again as defined for formula (I) but the dimethyl and diethyl variants are preferred. This group of compounds is for instance exemplified by the highly potentiating 2-amino-4-hydroxy-6-phenoxymethyl-7,7-dimethyl-7,8-dihydropteridine. The preparation of this and its analogues is described in the specification of U.K. patent application No. /72.

A third group within the scope of formula (I) is represented by compounds wherein R is limited to a halogeno substituted alkyl group with $R^1$ and $R^2$ as defined before. The halogen containing group is preferably mono- or dihalogeno substituted, most conveniently with bromine atoms. Particular compounds in this group are 2-amino-4-hydroxy-6-bromomethyl-7,7-dimethyl-7,8-dihydropteridine and the 6-dibromomethyl analogue, which are described, together with their analogues, in the specification of U.K. patent application No. /72.

Compounds of formula (I), and in particular DMHP, may not be very active by themselves against many bacteria such as Staphylococcus aureus, Streptococcus pyogenes, Streptococcus faecalis, Escherichia coli, Salmonella typhi, Proteus vulgaris, Pseudomonas aerugenosa, Pasteurella multocida among, others, but they exert a considerable potentiating effect on the activity of competitors and/or inhibitors. Thus by using an effective potentiating amount of a compound of formula (I) together with the competitor and/or the inhibitor, it is now possible to reduce significantly the amount of the competitor or the inhibitor required to inhibit the growth of these bacteria.

The methods mentioned above for the preparation of compounds of formula (I) involve in essence the reaction of a compound of formula (II), or a salt thereof,

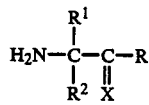

wherein R, R¹ and R² are as defined above, and X is a ketonic oxygen atom or a protecting group therefor, such as an oxime or thiosemicarbazone group, with 2-amino-4-chloro-6-hydroxy-5 nitropyrimidine, followed by removal of the protecting group, where appropriate, and reductive cyclisation of the resulting product. If necessary, substituent groups can be converted into different ones by the application of standard techniques in the art, for example the bromination of a 6-alkyl group to give the 6-bromoalkyl or 6-dibromoalkyl derivative.

Other pteridine potentiators within the broadest scope of the invention can be prepared by processes analogous to those described in the literature for various pteridines and to the above methods, or by interconversion of substituent groups by techniques well known and readily available to those skilled in the art.

Although the art is aware of many compounds which are known competitors of para-aminobenzoic acid and are antimicrobials, the sulphur compounds which are disclosed as antimicrobials agents beginning at the top of page 992 to page 1007 of Merck Index, 8th Edition, 1968 are presented by way of example only.

Of the known compounds which are competitors, the following sulphonamide compounds (or pharmaceutically acceptable salts thereof) are preferred for the purpose of this invention: sulfanilamide, sulfadiazine, sulfamethisazole, sulfapyridine, sulfathiazole, sulfamerazine, sulfamethazine, sulfisoxazole, sulformethoxine, sulfasomidine, sulfadimidine, sulfachlorpyridazine, sulfafurazole, 2-(p-aminobenzene)sulfonamido-3-methoxypyrazine(Kelfizina), α-amino-p-toluenesulfonamide, 5-sulfanilamido-2,4-dimethyl pyrimidine, 4-(N'-acetyl sulfanilamido)-5,6-dimethoxy pyrimidine, 3-sulfanilamido-4,5-dimethyl isoxazole, 4-sulfanilamido-5-methoxy-6-decyloxy pyrimidine, sulfamonomethoxine, 4-p-(8-hydroxy-quinilinyl-4-azo)-phenyl sulfanilamido-5,6-dimethoxy pyrimidine, sulfadimethoxine, sulfamethoxazole, sulfaquinoxaline, and p-(2-methyl-8-hydroxy-quinolinyl-(5)-azo)-phenyl sulfanilamido-5,6-dimethoxy pyrimidine, p-Amino salicylic acid (PAS) and p,p'-diaminodiphenylsulphone are examples of a non-sulphonamide type of competitor.

Similarly, although many compounds are known which inhibit dihydrofolic reductase and act as antimicrobial agents, the compounds disclosed in the following patents are presented by way of example of compounds suitable for use in this invention: U.S. Pat. Nos. 2,658,897; 2,767,183; 3,021,332; 2,937,284; 3,322,765; 2,909,522; 2,624,732; 2,579,259; 2,945,859; 2,576,939; 2,926,166; 2,697,710; 2,749,345 and 2,749,344.

The following inhibitors (or pharmaceutically acceptable salts thereof) are preferred for the purpose of this invention, however:

2,4-diamino-6-ethyl-5-p-chlorophenylpyrimidine (Pyrimethamine), 2,4-diamino-5-(3'4',5'-trimethoxybenzyl)pyrimidine (Trimethoprim), 2,4-diamino-5-(3',4'-dimethoxybenzyl) pyrimidine (Diaveridine), 2,4-diamino-5-(2'-isopropyl-4'-chlorophenoxy) pyrimidine, 2,4-diamino-5-methyl-6-sec-butylpyrido (2,3-d) pyrimidine, 2,4-diamino-5-methyl-6-benzylpyrido(2,3-d) pyrimidine, 2,4-diamino-6-benzylpyrido (2,3-d) pyrimidine, 2,4-diamino-5-6-trimethylenequinazoline, 2,4-diamino-5,6-tetramethylenequinazoline, 2,4-diamino-5-(2',4'5'-trimethoxybenzyl) pyrimidine, 2,4-diamino-5-(2'ethyl-4',5'-dimethoxybenzyl) pyrimidine, 2,4-diamino-5-(2'-methyl-4',5'-dimethoxybenzyl) pyrimidine.

However, the most preferred combinations include those combining DMHP with sulfadiazine, sulfamethoxazole, sulfadoxine or sulfaquinoxaline as competitors, or with trimethoprim, diaveridine or pyrimethamine as inhibitors. In view of possible synergistic advantages of using certain competitors and inhibitors in combination against particular diseases, and the potentiating effect of compounds of formula (I) on both these types of antibacterial compounds, it has been preferred to formulate triple combinations, comprising for instance DMHP with one of the above mentioned preferred competitors, and one of such inhibitors. For example, sulfadiazine/trimethoprim/DMHP or sulfamethoxazole/trimethoprim/DMHP, or sulfadoxine/trimethoprim/DMHP, or sulfaquinoxaline/diaveridine/DMPH have been shown to possess an improved effectiveness when compared with the components alone or with pairs of them.

The compounds of formula (I) together with the competitor and/or the inhibitor may be presented in association with a carrier in pharmaceutical formulations suitable for parenteral, topical, rectal or oral administration. The formulations for oral or rectal administration are advantageously presented in discrete units, such as tablets, capsules, cachets, ampoules or suppositories, each containing a predetermined amount of each compounds, but may also be presented as a powder, as granules, as a solution or suspension in an aqueous or non-aqueous liquid, or as an ointment or paste for topical administration. For parenteral use, the formulations incorporating an aqueous or non-aqueous liquid carrier must be sterile and be presented in sealed containers. The formulations may be made by any of the known methods and may include one or more of the following accessory ingredients: diluents, solutes to render the solution isotonic with the blood, buffers, flavouring, binding, dispersing, surfaceactive, thickening, lubricating and coating materials, preservatives, bacteriostats, antioxidants, suppository and ointment bases, and any other acceptable excipients.

Formulations containing the potentiator in association with a competitor or an inhibitor may also be presented in the form of a kit, which comprises separately packaged units or dosages of these components with instructions for use in a combined form. The instructions may also specify the manner of administration and indications for which the formula is suitable.

Any of the afore-mentioned compounds may be presented in the form of their pharmaceutically acceptable salts of a mineral or organic acid, for example hydrochloric acid, sulphuric acid, acetic acid, citric acid, lactic acid, maleic acid or salicylic acid, or, especially for the sulphonamide competitor, of a base, such as sodium or potassium hydroxide.

The ratios in which the therapeutically active compounds are utilized in the compositions, according to the present invention, can be varied between wide limits. Depending on the nature and circustance of use the compositions may contain the potentiator with the competitor and/or the inhibitor in appropriate proportions and dosages. For instance, in cases of uses in vivo it is often desirable to maintain a certain proportion of components in the blood serum or tissue fluids, preferably for a prolonged period. Depending on the various absorption, discharge or decomposition rates of the components, the initial quantities and proportions of the ingredients of the formulation can be different from that aimed at in the tissues in vivo. The formulations and dosages recommended for the general treatment of a particular human or animal disease must be adjusted according to the particular requirements of the recipients of the disease, the known activities of the competitor or inhibitor component against the causative organism, the half life and the toxicity of the components in vivo, and other practical requirements.

For example the composition or pharmaceutical formulation may contain from about 1 to 30 parts, preferably 5 to 15 parts, of the potentiator, e.g. a compound of formula (I), or an equivalent amount of a salt thereof, and 1 to 30 parts, preferably 5 to 15 parts, of a competitor, or an equivalent amount of a salt thereof, and/or one part of an inhibitor, or an equivalent amount of a salt thereof. Dosage will vary depending upon the infecting organism. However, under ordinary circumstances up to about 60 mg/kg each of potentiator and competitor, and up to about 7.5 mg/kg of inhibitor, in combination, can be administered daily in several doses.

The composition or pharmaceutical formulation can be administered to human patients in unit dosage forms which contain up to 750 mg of the potentiator compound of formula (I), and up to 750 mg of the competitor and/or up to 25 mg of the inhibitor. Preferably for adult dosages the amount of the potentiator would be about 200 mg that of the competitor about 200 mg and/or that of the inhibitor about 25 mg.

The pharmaceutical formulation comprising the compound of formula (I) in combination with the competitor and/or the inhibitor is also usable in solution for irrigating wounds, for example after surgery, so as to prevent the growth of bacteria. For example, an antibacterial solution having the following preferred concentration of components may be used: 1–30 mg/ml of the compound of formula (I), 1–30 mg/ml of the competitor and/or 0.03–1 mg/ml of the inhibitor, in a pharmaceutically acceptable solvent, suitable for external use.

The potentiating effect of compounds of formula (I) can be demonstrated and utilized in vitro relatively easily for research and practical purposes. Such possibilities include diagnosis and the identification of the bacterial flora of individuals and the consequential selection of clinical treatment schedules.

The compositions of this invention are useful in the treatment of infections caused by microorganisms e.g. *Staphylococcus aureus, Pseudomonas aerugenosa* and *Pasteurella multocida*.

The various combinations can be incorporated in porous discs (such as filter paper discs) or in Agar Nutrient or other media for bacterial growth for determining susceptibility. Those articles incorporating the potentiator compound with a competitor and/or an inhibitor compound may be distributed or sold to doctors, hospitals and clinics for the above purposes. A typical testing disc may be impregnated with a solution containing 5 to 50 µg/ml of a para-aminobenzoic acid competitor, 0.5 to 5 µg/ml of a dihydrofolic reductase inhibitor, and about 10 to 100 µg/ml of DMHP in a medium comprising a mixture of an aqueous infusion and papain digest of horse muscle.

Furthermore, such pharmacological tests involving potentiated competitors or inhibitors may also be useful for the characterisation of bacteria according to their sensitivity and to their particular resistance for instance to a competitor when used alone, and such investigations involving a variety of formulations according to the present invention also form the basis of determining the compositions of selected formulations for general treatment purposes. The toxicity of compounds of formula (I) is generally considerably lower than that of the competitors or inhibitors commonly used, which may enable the clinician to maintain or increase the effectiveness of the antibacterial activity of the formulation with a concurrent increase of the therapeutic ratio or decrease in the toxic or side-effects of the medicament.

In addition to the anti-bacterial activity of the aforementioned competitors and inhibitors in man and in vitro, they have already been used against infections with microorganisms in domestic animals, including poultry, for example against *Pasteurella multocida* but especially against the protozoal disease coccidiosis. Coccidiosis is a disease of considerable economic importance in domestic animals throughout the world, particularly in all forms of poultry, and is caused by members of the genera Eimeria and Isopora of the taxonomic group Coccidia. Two common types of this infection are known: the acute or 'caecal' caused by the coccidium *Eimeria tenella* and characterised by a severe haemorrhage on or about the 5th day of infection, and the chronic or 'intestinal' caused by several types of Eimeria species, including *E. acervulina, E. necatrix, E. maxima* and *E. brunetti*.

For example it is known that certain sulphonamides such as sulphamethazine, sulphadiazine sulphadimethoxine, and especially sulphaquinoxaline are active against coccidiosis in poultry, although the therapeutic dose required can give rise to toxic side-effects. It is further known that certain 2,4-diamino-5-benzyl-or-5-phenyl-pyrimidines, in particular the 5-substituted (3'-lower alkoxybenzyl) pyrimidines and especially 2,4-diamino-5-(3'4' dimethoxybenzyl) pyrimidine, hereinafter referred to as 'diaveridine', are effective against this disease. Although pyrimidine inhibitors of bacterial metabolism are generally more expensive to produce than the sulphonamides, they synergise the sulphonamides with the result that smaller quantities of the mixture are efficacious against the disease, the effective dose of sulphonamide being reduced by a factor of up to 10.

Potentiators according to the present invention, and in particular the compounds of formula (I), can be combined with advantage with competitors and inhibitors which are active against coccidiosis to provide an effective triple combination, and in some instances the compounds of formula (I) may be active alone, for example against *E. acervulina*.

The combination of sulfaquinoxaline with diaveridine and DMHP has been found particularly active against coccidiosis in poultry particularly in chickens. Such a triple formulation is effective in lower concentrations than the sulfonamide or pyrimidine components alone, and gives a better control of the infection and possesses an activity increase three to four fold over previously known compositions. It has, furthermore, the advantage of an overall satisfactory effectiveness against all relevant Eimeria species causing this disease in poultry.

The compounds of the formulation against coccidiosis can preferably be presented alone or in combination as an additive to be mixed with the bird's food or drink. This additive may be a concentrated food 'pre-mix' or drink additive which contains the required compounds in a diluted form compared with the compounds alone but in a more concentrated form than will be administered to the bird.

As a food 'pre-mix', the compounds together with any other compatible active agents such as antibiotics, vitamins or minerals which are required are mixed with carriers or diluents such as bran, ground maize, barley or other corn, wheat shorts, husks, edible vegetable substances, flour, soya bean flour, crumbs and similar foodstuffs and possibly other diluents such as crushed limestone and grits, and the components are thoroughly mixed by conventional techniques such as grinding, stirring, milling or tumbling. The mixture is then presented as a powder or other small particulate composition or it may be further processed into pellets or similar food additives. This food 'pre-mix' is then added to other foods at the concentration of say 1 lb of pre-mix per cwt. of food, depending on the concentration of the active components in the pre-mix. Alternatively ready mixed foods containing the compounds in a form suitable for direct administration to the birds may be produced.

If the compounds are presented as drink additives they are normally in the form of their acid addition salts. These may be presented in a finely divided solid form, optionally together with other soluble additives, or they may be presented as a 'concentrate' containing the compounds in solution in suitable solvents. This powder or concentrate is then added to the drinking water. This method of presentation in the form of a drink additive is not as suitable as a food additive because the uptake of drink by poultry is more variable then food intake.

Concentrations around 30 to 100 parts per million (p.p.m) (i.e. 0.003 to 0.01%) of the potentiator in the diet of the birds, in combination with 10 to 60 parts of diaveridine or sulphaquinoxaline already shows an improved effect, but best results are obtained with triple combinations of these components. Although a wide range of concentrations of components in such triple combinations may be suitable, relative concentrations of about 5 to 250 p.p.m of potentiator, preferably 10 to 90 p.p.m. and about 10 to 100 p.p.m of each of diaveridine and sulphaquinoxaline preferably 15 to 60 p.p.m, are especially effective. Whilst at low total drug concentrations a 1:1 or 2:1 concentration ratio of sulphaquinoxaline to diaveridine is particularly preferred, this ratio may satisfactorily be increased to a 4:1 ratio at higher concentrations of total drug.

Replacement of DMHP by its 6-methyl analogue produced a noticeable, athough less marked potentiating effect against coccidiosis.

According to the present invention, therefore, there are provided in further and particular aspects, (a) a composition, as hereinbefore defined, in which the potentiator is a pteridine compound, such as a 2-amino-4-hydroxy-7,8-dihydropteridine substituted on the 6th-position through a carbon atom and disubstituted at the 7th-position. In particular, the composition comprises a compound of formula (I), as hereinbefore defined, especially one with a dimethyl or diethyl substitution in the 7th-position.

(b) a composition, as specified under (a), which comprises the compound of formula (I), wherein R is a 6-alkyl or a 6-hydroxyalkyl group. The alkyl group is preferably a methyl group;

(c) a composition as specified under (a), which comprises a compound of formula (I), wherein R is a phenoxyalkyl group, especially a phenoxymethyl group;

(d) a composition a specified under (a) which comprises a compound of formula (I) wherein R is a halogeno sutstituted alkyl group. In particular, mono- or di-substituted compounds are preferred in this respect, especially with bromine substituents;

(e) a composition, as hereinbefore defined in any aspect, comprising an effective potentiating amount of a potentiator, in combination with an effective amount of both a competitor and an inhibitor;

(f) a pharmaceutical formulation containing any one of the above defined compositions in combination with a pharmaceutically acceptable carrier therefor;

(g) a pharmaceutical formulation as defined under (f) in the liquid form, for use in the inhibition of the production of dihydrofolic acid by microorganisms, under in vitro or in vivo conditions.

(h) a pharmaceutical formulation, as hereinbefore defined, presented in the form of a kit of separately packaged potentiator, inhibitor or competitor, with instructions to use them together in combination for the purpose of medical or veterinary treatment.

(i) a pharmaceutical formulation for the testing or treatment of coccidial systems and infections, comprising an effective potentiating amount of DMHP, in combination with effective amounts of sulphaquinoxaline and diaveridine.

(j) a method of making a composition or a pharmaceutical formulation, as hereinbefore defined, in which the effective amounts of the appropriate components are admixed and presented in a combined form;

(k) a method of treating and preventing microbial infections comprising the administration to the host of any one of the compositions or pharmaceutical formulations hereinbefore defined.

(l) a method of inhibiting the production of dihydrofolic acid by microorganisms which comprises contacting the microorganism with a composition or pharmaceutical formulation hereinbefore defined.

EXAMPLE 1

Potential pteridine antagonists may be tested by investigating the inhibitory effect they impose on the enzymes responsible for the biosynthesis of dihydropteroic acid (DPtA), namely hydroxymethyldihydropteridine pyrophosphokinase (HMPPS), and dihydropteroate synthetase, hereinafter referred to as 'synthetase'.

(1) HMPPS

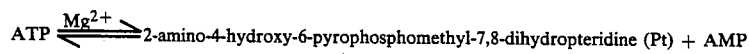

(2) Synthetase

Pt + p-aminobenzoic acid (pAB) $\xrightleftharpoons{Mg^{2+}}$ dihydropteroic acid (DPtA) + pyrophosphate (a) An assay for HMPPS was developed in which the transfer of the terminal phosphate of ATP-$\gamma$-P$^{32}$ to Pt could be monitored and correlated with the amount of inhibition of HMPPS by the compound under test.

The compound under test was incorporated into various formulations comprising metabolites and enzymes contained in test tubes, as indicated in TABLE 1.

The components of the mixture were as follows:

I—2-amino-4-hydroxy-6-hydroxymethyl-7,8-dihydropteridine (HMPt) in a concentration of 800 $\mu$M i.e. micromoles;

II—a source of HMMP S, obtained from an extract of E. coli and separated from 'synthetase' on Sephadex G-100, according to the method of Richey and Brown in J. Biol. Chem. 244, 1582-1592 (1969)

III—3 mM ATP-$\gamma$-P$^{32}$.

IV—0.10M ATP neutralised (unlabelled).

V—0.02M MgCl$_2$.6H$_2$O.

VI—0.1M MgCl$_2$.6H$_2$O.

VII—Source of HMPPS and 'synthetase'

VIII—the test compound in a concentration of $0.93 \times 10^{-3}$M

IX—0.4 mM pAB-C$^{14}$

As shown in TABLE 1, tubes 1 to/all contain a source of HMPPS, labelled ATP and 0.02M MgCl$_2$.6H$_2$O, tubes 2 to 9 containing in addition HMPt and tubes 4 to 9 further containing the test compound. Control tubes 10 to 12 include a source of both HMPPS and synthetase, unlabelled ATP, 0.1M MgCl$_2$.6H$_2$O and labelled pAB.

Tubes 1 to 9 containing the amounts of components shown in the Table, were filled up to 200 $\mu$l with distilled water, incubated for 60 minutes at 37° C. and then chilled on ice. Dextrose (20 $\mu$l containing 72.1 mg/ml) and hexokinase (5 $\mu$l containing 2000 units/ml) were added to the solution, which was then allowed to stand at room temperature for 15 minutes. 'Darco-G-60' (Registered Trade Mark) (10 mg) was added to each tube and the contents mixed periodically for 10 minutes. The charcoal was removed through a "Millipore AP 250 2200" (Registered Trade Mark) filter and the filter was washed with three 10 ml portions of cold water. The Charcoal and the filter were then radioactively counted.

The radioactive count from the contents of tubes 2 and 3 was taken as the maximum count, since these tubes contained no test compound and thus gave 0% enzyme inhibition. The percentage inhibition produced by the contents of the remaining tubes could then be calculated by relating their radioactive count to the maximum, as determined above.

The contents of tubes 10 to 12 were chromatographically analysed as described under part (b), and used as controls, tubes 10 and 11 containing no test compound (and hence giving 0% inhibition) being accorded the value of 100. The percentage inhibition exhibited by the contents of the tubes in part (b) of the experiment could then be calculated in relation to this, by comparing the respective chromatograms.

(b) The activity of the test compound against 'synthetase' was determined as follows, by monitoring the formulation of dihydropteroate-C$^{14}$.

A pool of Pt was prepared from ATP neutralised (50 $\mu$l, 0.1M), MgCl$_2$.6H$_2$O (50 $\mu$l, 0.1M), dithiothreitol (100 $\mu$l, 0.1M), tris buffer (100 $\mu$l, 0.4M, pH 8.3), HMPt (25 $\mu$l, 876 $\mu$M) and 170 $\mu$l of a solution containing HMPPS. The mixture was incubated for 60 minutes at 37° C., chilled briefly on ice and then dextrose (100 $\mu$l containing 72.1 mg/ml) and hexokinase (20 $\mu$l containing 2000 units/ml) were added at room temperature to the solution, which was allowed to stand at this temperature for 15 minutes.

A solution of MgCl$_2$.6H$_2$O (10 $\mu$l, 0.1M), pAB-C$^{14}$ (10 $\mu$l, 0.4 mM), dithiothreitol (20 $\mu$l, 0.1M) and tris buffer (20 $\mu$l, 0.4M, pH8.3) was made in each of five test tubes and then 80 $\mu$l of the contents of the pool added to each, together with synthetase and/or test compound as indicated in TABLE 2. The solution was then made up to 200 $\mu$l with distilled water.

Two control test tubes were prepared, each containing ATP (10 $\mu$l, 0.1M), MgCl$_2$.6H$_2$O (10 $\mu$l, 0.1M), dithiothreitol (20 $\mu$l, 0.1M) tris buffer (20 $\mu$l, 0.4M, pH 8.3), pAB-C$^{14}$ (10 $\mu$l, 0.4 mM), and 20 $\mu$l of a solution containing HMPPS and 'synthetase' of known activity. The test compound was added to the second of these two tubes up to a final concentration of 10$^{-5}$M, and both tubes were made up with distilled water to 200 $\mu$l.

All seven tubes were then incubated for 30 minutes at 37° C., chilled on ice and then these, together with control tubes 10 to 12 from part (a), were chromatographically analysed as follows:

100 $\mu$l of the contents of each of the tubes was spotted onto Whatman No. 3 MM chromatography paper (2$\times$20 cm) at the 'origin', the run descending in a Sørenson buffer of potassium and sodium phosphates (0.1M, pH 7.0) for 10 to 15 cm. From the relative positions of the spots obtained from the contents of the different tubes, the various percentage inhibitions of synthetase could be evaluated by reference to control tubes 10 and 11, which gave 0% inhibition.

Column (X) of TABLE 1 and the fourth column of TABLE 2 give the percentage inhibition shown with DMHP as the test compound.

Those compounds which, as result of these tests, were found to give 50% inhibition at a concentration of 100 $\mu$M or less, are those which exert a useful potentiating effect, and subject to their toxicity being favourable, may be included in the compositions of the present invention.

The results of the inhibition exerted by the preferred potentiators of this invention are shown in TABLE 3.

EXAMPLE 2

"Screening tests" were performed to establish the effectiveness of the compounds of formula (I) both alone and in combination with a competitor and or an inhibitor and to determine the most useful levels of relative concentrations of each component in combatting or suppressing coccidiosis.

Groups of Ranger cockerels, housed in small, heated cages with wire floors situated in environmentally controlled isolation rooms, were infected orally with sporulated oocysts of the Eimeria spp such as E. tenella or E. acervulina. The appropriate test compound(s), (DMHP, sulphaquinoxaline (SQX) or diaveridine (DV) or any combination of these) were incorporated in a small quantity of specially formulated laboratory ration deficient in Vitamin K ('L.D.4 mash'), as a 1/10 pre-mix, which was then mixed into the diet on a horizontal roller drum mixed and administered to groups of chicks one day prior to infection, leaving some groups as untreated controls. Administration was continued for several days, for example about 8 or 9 days.

The amount of damage, marked by lesions in the caecal walls was investigated in those chicks that died during the course of the experiment, and in those sacrificed on the final day of administration, and compared with the untreated controls as a basis for the determination of therapeutic activity. In addition the mortality rate and the percentage weight gains in the various groups were assessed. A marked or definite effect of the administered drug could be recognised even when the mortality rates were similar or identical, since the increase in the weight gains and the reduction of the extension of lesions indicated by the lesion score, is characteristic of an improvement.

Experiment 1

Groups of 5, one-week old chicks were infected orally with 200,000 sporulated oocysts of the Weybridge strain of *E. tenella*. One day prior to this infection, administration of DMHP, in concentrations of 10, 30, 90 or 250 parts per million of diet (p.p.m.) alone and in combination with a mixture of diaveridine (30 p.p.m) and sulphaquinoxaline (30 p.p.m) was effected and continued for 8 days. Mortality from coccidiosis and lesions, measured 6 days after infection, and the weight gain of the group of birds from the day of infection to the 6th day post infection were assessed and compared with the untreated controls.

Experiment 2

Groups of 10, one-week old chicks were infected with 200,000 sporulated oocysts of the Weybridge strain of *E. tenella* and, in accordance with the procedure of Experiment 1, diaveridine/sulphaquinoxaline mixtures at levels of 60/60 30/30, 15/15 and 7.5/7.5 p.p.m were administered alone and in combination with DMHP at a concentration of 100 p.p.m. to the birds to determine the potentiating effect of DMHP.

Experiment 3

Groups of 10, one-week old chicks were infected with 100,000 sporulated oocysts of *E. tenella*, and a sub-optimal combination (15/15 p.p.m.) of diaveridine/suphaquinoxaline was administered alone and in combination with DMHP at concentrations of 3, 10, 30 and 90 p.p.m.

Experiment 4

Group of 10, one-week old chicks infected with 100,000 sporulated oocysts of *E. tenella* and various combinations of diaveridine (10, 20 p.p.m), sulphaquinoxaline (20, 40 p.p.m) and DMHP (10, 20 p.p.m) were administered, each component singly and together with either one or both other components, in order to ascertain whether DMHP produced more marked potentiation with the pyrimidine or the sulphonamide component.

Experiment 5

Groups of 5, one-week old chicks were infected with 100,000 sporulated oocysts of *E. tenella*. Mixtures of 5 ratios of diaveridine/sulphaquinoxaline from 1:1 to 5:1 at suboptimal concentrations (40 p.p.m. total) combined with DMHP at 4 levels from 5 to 40 p.p.m were administered to determine the optimal proportion of the three components and therefore the smallest amounts of drug required.

Experiment 6

Groups of 5, three-week old chicks were infected with 500,000 sporulated oocysts of the Weybridge strain of *E. acervulina* and the procedure of Experiment 1 was followed, administration of the test compound(s) being continued for 9 days. Mortality from coccidiosis and lesions and the total oocyst output per bird over the 5th, 6th and 7th days after infection and the weight gain from the day of infection to the 7th day after infection was assessed.

Experiment 7

Groups of 5, three-week old chicks were infected as in Experiment 6 and one day prior to infection, DMHP in concentrations of 5, 10, 30 or 90 p.p.m of diet alone and in combination with a mixture of diaveridine (10 p.p.m) and sulphaquinoxaline (10 p.p.m) was administered and continued for 9 days.

Experiment 8

Groups of 5, three-week old chicks were infected with 5,000,000 sporulated oocysts of the Weybridge strain of *E. acervulina* and the procedure of Experiment 7 was followed except that DMHP was only administered at concentrations of 5, 10 and 30 p.p.m.

Experiment 9

Groups of 5, one-week old chicks were infected with 100,000 sporulated oocysts of the Weybridge strain of *E. tenella* and, in accordance with the procedure of Example 1, 4:1 sulphaquinoxaline/diaveridine mixtures at levels of 80/20, 60/15, 40/10 and 20/5 p.p.m. were administered alone and in combination with a wide range of low concentrations of DMHP to the birds.

The results of these screening tests are set forth in Table 4 showing the concentration of the various component compounds in parts per million of the bird's diet, the mortality from coccidiosis, the percentage weight gain, the lesion score the oocyst output, and the activity. The caecal lesion index is calculated using a score system where:

0 = no lesions

1 = few haemorrhages, no thickening of caecal wall

2 = moderate haemorrhages, some thickening of caecal wall

3 = numerous haemorrhages with caecal cores present

4 = numerous haemorrhages, caeces enlarged with large cores

In addition a score of 4 is assigned to any bird that dies of coccidiosis during the experiment.

The caecal lesion index =

$$\frac{\text{(The total lesion score of the survivors)} + (4 \times \text{no. of deaths)}}{\text{Original number of birds}}.$$

In the activity column, +++, ++, +, ± and − relate respectively to very high, high, slight, doubtful and nil activity of the test drug against the Eimeria infection.

Results

The Experiments showed that whilst DMHP alone was inactive at all levels of concentration tested against infection with *E. tenella*, DMHP potentiated the activity of the majority of the diaveridine/sulphaquinoxaline mixtures tested, in many cases by as much as 3 to 4 fold, giving better control of the infection, a marked reduction in caecal lesions and restoration of the weight of the birds to their pre-infection values Although a reduction in activity was observed as the concentration of DMHP was lowered, its inclusion in combination even at the 10. p.p.m level showed a marked improvement in the activity, whilst a reduction in the lesion score was observed with a 4:1 sulphaquinoxaline/diaveridine mixture on the addition of only 5 p.p.m of DMHP.

There was found to be little potentiation of either diaveridine or sulphaquinoxaline alone by the addition of DMHP at the levels tested in the treatment of *E. tenella* infection, and it appeared that the triple mixture was necessary for good activity, although the possibility was not ruled out of potentiation of a single component at other concentration levels.

A wide variation in relative concentrations of the three components produced favourable activities, but the combinations found to be particularly effective were these hereinbefore mentioned, namely those comprising 15 to 60 p.p.m of sulphaquinoxaline, 15 to 60 p.p.m of diaveridine, and 10 to 90 p.p.m of DMHP. Preferred concentration ratios of sulphaquinoxaline/diaveridine were 1:1 or 2:1 at low total drug concentrations or up to 4:1 at higher levels.

In the Experiments carried out with moderate infection with the intestinal species *E. acervulina* it was found that DMHP was active alone at concentrations of 250 and 90 p.p.m although below this level the activity declined as shown by a depression in the percentage weight gain and an increase in oocyst output. Similary a 10 p.p.m. diaveridine/10 p.p.m. sulphaquinoxaline mixture was relatively inactive alone but the addition of DMHP gave a marked increase in activity which was sustained at the lowest concentration of DMHP used.

An increase by one order of magnitude in the number of oocysts of *E. acervulina* used as the source of infection resulted in inactivity of both DMHP alone and a 10 p.p.m diaveridine/10 p.p.m. sulphaquinoxaline mixture. Triple potentiation was demonstrated by the addition of DMHP to the mixture with the infection controlled at all levels of DMHP tested.

EXAMPLE 3

A further experiment was conducted to investigate whether a compound of formula (I) potentiated either a competitor and/or an inhibitor in combatting or suppressing bacterial infection with *Pasteurella multocida*.

Experiment 1

Groups of 10 chicks were infected orally with $8 \times 10^6$ organisms of *Pasteurella multocida* and, two days prior to this, administration was commenced of 85/15 sulphaquinoxaline/diaveridine mixtures alone and in combination with DMHP in the ratio of 50/20, 50/10, 50/5, 25/20, 25/10, and 25/5 p.p.m of the diet, leaving some groups untreated as controls. Cumulative mortality from the date of infection and weight gain as a percentage of uninfected controls were assessed and the results are show in Table 5.

Experiment 2

An exeriment was carried out following the procedure of Experiment 1 in which, however, 85/15 mixtures of sulphaquinoxaline and trimethoprim, (TMP), were combined with DMHP in the ratios 25/20, 25/10, 25/5, 12.5/20, 12.5/10 and 12.5/5. The cumulative mortality from the date of infection is shown in Table 6.

From the results of Experiment 1 it seen that diaveridine had low activity alone and had very little potentiating effect on sulphaquinoxaline, which had good activity alone. The addition of DMHP, however, even at 5 p.p.m in the food, produced a marked increase in activity of the diaveridine/sulphaquinoxaline mixture. In the second Experiment a smaller potentiating effect by DMHP on the combination of trimethoprim and sulphaquinoxaline was observed at the dosages used.

EXAMPLE 4

In further experiments investigating the antibacterial activities of sulphamethoxazole and trimethoprim when combined with DMHP either singly or as a triple combination, DMHP potentiated the individual activities of sulphamethoxazole and trimethoprim against *Staphylococcus aureus* and further enhanced the synergy of these drugs when acting together. Table 7 summarises the results of an experiment conducted in Wellcome Nutrient Agar, incubation being continued for 18 hours at 37° C.

EXAMPLE 5

The potentiation by DMHP was also demonstrated by the accentuation of the inhibitory effects of trimethoprim and sulphamethoxazole on the growth rate, measured turbidometrically, of *Staphylococcus aureus* N 491 during a 7-hour incubation period in Wellcome Nutrient Broth at 37° C. In these experiments sub-effective doses of trimethoprim and sulphamethoxazole were used, and the percentage of inhibition is shown in Table 8.

EXAMPLE 7

In this experiment the effects of DMHP on the bactericidal activity for *Staphylococcus aureus* of trimethoprim and sulphamethoxazole, singly and in combination, were determined.

The results are shown in Table 9 in which the bactericidal activity is expressed as the percentage of the original inoculum, measured by viable counts, which was alive after 24-hours' incubation at 37° C. The inoculum used gave a final concentration of $10^6$ organisms per ml.

In this test, although neither trimethoprim at 1.0 μg/ml nor sulphamethoxazole at 10 μg/ml was bactericidal in the absence of DMHP, both were very active when 10 μg/ml of DMHP was present. Furthermore the bactericidal activity of the combination of 0.1 μg sulphamethoxazole per ml was definitely increased when 10 ∞g/ml DMHP was present.

EXAMPLE 8

In this experiment inhibitor zone data were determined to evaluate the synergistic activity of DMHP or its 7,7-diethyl analogue on its combination with trimethoprim (TMP) and/or sulphamethoxazole (SMX) against *Staphylococcus aureus* and *Pseudomonas aeruginosa*.

The pteridine was included in a soya peptone medium of low thymidine content (Wellcotest Sensitivity Test Agar) contained in a Petri-dish and the other component(s) added to the well resulting from the removal of a small plug from the medium. The surface of the medium was inoculated with the test organism and then incubated. The amount of zone inhibition is shown in Table 10, wherein the numbers represent the complete zone inhibition (i.e. the number of centimeters from the edge of the well after about 6×magnification) and the figures in parentheses include the zones of partial inhibition.

The Results show that both compounds show synergism with TMP and SMX alone and multiple synergism with both against *Staphylococcus aureus*, the diethyl analogue being slightly more active than DMHP. Potentiation agains *Pseudomonas aeruginosa* is also observed with DMHP, showing the higher potentiation against this organism.

EXAMPLE 9

Further experiments also demonstrated on a standard nutrient medium the utility of testing discs of formulations containing the potentiator together with an inhibitor and/or competitor of bacterial growth. The results are shown in Table 11.

EXAMPLE 10

In this experiment mice were infected intraperitoneally with *Staphylococcus aureus* suspended in 3% hog stomach mucin. Groups of the animals were treated orally (P.O.) and intraperitoneally (I.P.) with trimethoprim and sulphamethoxazole, singly and together, with and without DMHP, twice daily for three days. The results which are given in Table 12 show that DMHP enhances the protection afforded by TMP and SMX.

EXAMPLE 11

The effect of DMHP on the activity of pyrimethamine alone or in combination with sulphamethoxazole was tested in mice infected with protozoa of *Toxoplasma gondii*.

The experimental mice were infected with 0.5 ml of a $10^{-3}$ exudate of mice (5000 protozoa), which represented approximately 1000 $LD_{50}$ doses. The treatment was carried out by administering the compound or the combination immediately after infection, then 6 hours later, and again at 24 and 48 hours later. Results on Table 13 show that DMHP potentiates the antiprotozoal action of both pyrimethamine alone and when in combination with sulphamethoxazole.

EXAMPLE 12

| Tablet Formulation | |
|---|---|
| DMHP (pure) | 100 mg |
| Trimethoprim (pure) | 25 mg |
| Sulfaguanidine(B.P.C.) + | 100 mg |
| cornstarch, lactose, gelatin, talcum and magnesium stearate | |

Preparation:
the above constituents were mixed together using known methods of pharmacy to form a granulation which was then compressed into tablets.

EXAMPLE 13

| Tablet Formulation | |
|---|---|
| "Pyremathimine" (Pyrimethamine) B.P. | 15 mg |
| DMHP(pure) | 150 mg | which was then prepared to form a tablet as in Example 12.

EXAMPLE 14

| Tablet Formulation | |
|---|---|
| Sulfanilamide B.P.C | 150 mg |
| DMHP (pure) | 175 mg | which was then prepared to form a tablet as in Example 12.

EXAMPLE 15

| Capsule Formulation | |
|---|---|
| Trimethoprim (pure) | 20 mg |
| DMHP (pure) | 100 mg |

Preparation:
The compounds in granular form were blended together with lactose, cornstarch and magnesium stearate. The powder was filled into a two-piece, hard shell gelatin capsule using a capsulating machine.

EXAMPLE 16

| Irrigant Solution | |
|---|---|
| DMHP (pure) | 1 mg/ml |
| Trimethoprim (pure) | 0.2 mg/ml |
| Solvent | water |

EXAMPLE 17

| Irrigant Solution | |
|---|---|
| DMHP (pure) | 2 mg/ml. |
| α-amino-p-toluenesulphonamide(pure) | 2 mg/ml |

EXAMPLE 18

| SOLUTION | |
|---|---|
| DMHP (pure) | 1.5 mg/ml. |
| Diaveridine B. Vet C | 0.5 mg/ml |
| Kelfizina | 1.0 mg/ml |
| Solvent | water |

TABLE 1

| Tube No. | I | II | III | IV | V | VI | VII | VIII Final Concn. | IX | X % Inhibn. |
|---|---|---|---|---|---|---|---|---|---|---|
| 1 | — | 100 μl | 15 μl | — | 10 μl | — | — | — | — | — |
| 2 | 5 μl | " | " | — | " | — | — | — | — | — |
| 3 | " | " | " | — | " | — | — | — | — | — |

TABLE 1-continued

| Tube No. | I | II | III | IV | V | VI | VII | VIII Final Concn. | IX | X % Inhibn. |
|---|---|---|---|---|---|---|---|---|---|---|
| 4 | " | " | " | — | " | — | — | $2.5 \times 10^{-16}$ M | — | 44 |
| 5 | " | " | " | — | " | — | — | " | — | 33 |
| 6 | " | " | " | — | " | — | — | $1 \times 10^{-5}$ M | — | 87 |
| 7 | " | " | " | — | " | — | — | " | — | 55 |
| 8 | " | " | " | — | " | — | — | $0.93 \times 10^{-4}$ M | — | 98 |
| 9 | " | " | " | — | " | — | — | " | — | 95 |
| Controls | | | | | | | | | | |
| 10 | — | — | — | 10 μl | — | 10 μl | 20 μl | — | 10 μl | — |
| 11 | 5 μl | — | — | " | — | " | " | — | " | — |
| 12 | " | — | — | " | — | " | " | $1 \times 10^{-5}$ M | " | 79 |

TABLE 2

| Tube No. | Synthetase | Test compound Final Concentration | % Inhibn. |
|---|---|---|---|
| 1 | — | — | — |
| 2 | + | — | — |
| 3 | + | $8.7 \times 10^{-5}$ M | 9 |
| 4 | + | $1 \times 10^{-5}$ M | 0 |
| 5 | + | $2.5 \times 10^{-6}$ M | 5 |
| Controls | | | |
| 6 | — | — | — |
| 7 | — | $1 \times 10^{-5}$ M | 83 |

TABLE 3

| Test Compound | | | $IC_{50}$ (μm) |
|---|---|---|---|
| R | $R^1$ | $R^2$ | |
| $CH_2OH$ | Me | Me | 2–4 |
| Me | Me | Me | 75 |
| $CH_2Br$ | Me | Me | 5 |
| $CHBr_2$ | Me | Me | 25 |
| $CH_2OH$ | Et | Et | 2.1 |

TABLE 4

| Expt. | Treatment | Concn. SQX in diet p.p.m | Concn. DV in diet p.p.m | Concn. DMHP in diet p.p.m | Mortality from Coccidiosis | % Wt Gain | Lesion Score | Activity |
|---|---|---|---|---|---|---|---|---|
| 1 | Uninfected untreated control | | | | 0/5 | 100 | 0.0 | |
| | Infected untreated control | | | | 2/5 | 26 | 3.4 | |
| | DMHP | — | — | 250 | 1/5 | 29 | 3.0 | — |
| | DMHP | — | — | 90 | 2/5 | 36 | 3.2 | — |
| | DMHP | — | — | 30 | 3/5 | 45 | 3.4 | — |
| | DMHP | — | — | 10 | 3/5 | 40 | 3.4 | — |
| | SQX + DV | 30 | 30 | — | 0/5 | 90 | 1.6 | ++ |
| | SQX + DV + DMHP | 30 | 30 | 250 | 0/5 | 96 | 0.0 | +++ |
| | SQX + DV + DMHP | 30 | 30 | 90 | 0/5 | 89 | 0.0 | +++ |
| | SQX + DV + DMHP | 30 | 30 | 30 | 0/5 | 89 | 0.0 | +++ |
| | SQX + DV + DMHP | 30 | 30 | 10 | 0/5 | 79 | 1.0 | ++ |
| 2 | Uninfected untreated control | | | | 0/10 | 100 | 0.0 | |
| | Infected untreated control | | | | 6/10 | 31 | 3.6 | |
| | SQX + DV | 60 | 60 | — | 0/9 | 91 | 0.1 | +++ |
| | SQX + DV | 30 | 30 | — | 0/9 | 78 | 2.2 | + |
| | SQX + DV | 15 | 15 | — | 6/10 | 42 | 3.4 | — |
| | SQX + DV | 7.5 | 7.5 | — | 6/9 | 22 | 3.9 | — |
| | SQX + DV + DMHP | 60 | 60 | 100 | 0/10 | 100 | 0.0 | +++ |
| | SQX + DV + DMHP | 30 | 30 | 100 | 0/10 | 104 | 0.0 | +++ |
| | SQX + DV + DMHP | 15 | 15 | 100 | 0/10 | 98 | 0.2 | +++ |
| | SQX + DV + DMHP | 7.5 | 7.5 | 100 | 0/9 | 67 | 2.5 | + |
| 3 | Uninfected untreated control | | | | 0/10 | 100 | 0.0 | |
| | Infected untreated control | | | | 6/10 | 4 | 3.7 | |
| | SQX + DV | 15 | 15 | — | 4/9 | 42 | 3.3 | — |
| | SQX + DV + DMHP | 15 | 15 | 90 | 0/10 | 95 | 0.0 | +++ |
| | SQX + DV + DMHP | 15 | 15 | 30 | 0/9 | 100 | 1.0 | ++ |
| | SQX + DV + DMHP | 15 | 15 | 10 | 0/9 | 61 | 2.6 | + |
| | SQX + DV + DMHP | 15 | 15 | 3 | 3/10 | 31 | 3.3 | — |
| 4 | Uninfected untreated control | | | | 0/10 | 100 | 0.0 | |
| | Infected untreated control | | | | 6/10 | 11 | 3.6 | |
| | DV | 10 | — | — | 8/10 | 18 | 3.8 | — |
| | SQX | — | 20 | — | 8/10 | 5 | 3.8 | — |
| | DMHP | — | — | 10 | 8/10 | 16 | 3.8 | — |
| | DV + DMHP | 10 | — | 10 | 8/9 | −1 | 3.7 | — |
| | SQX + DMHP | — | 20 | 10 | 5/9 | 15 | 3.2 | — |
| | SQX DV | 10 | 20 | — | 7/10 | 27 | 3.8 | — |
| | SQX DV + DMHP | 10 | 20 | 10 | 3/10 | 26 | 3.4 | — |
| | DV | 20 | — | — | 8/9 | 18 | 3.8 | — |

TABLE 4-continued

| | | Concn. SQX in diet p.p.m | Concn. DV in diet p.p.m | Concn. DMHP in diet p.p.m | Mortality from Coccidiosis | % Wt Gain | Lesion Score | Activity |
|---|---|---|---|---|---|---|---|---|
| | SQX | — | 40 | — | 9/10 | 20 | 3.9 | — |
| | DMHP | — | — | 20 | 6/10 | 20 | 3.6 | — |
| | DV + DMHP | 20 | — | 20 | 1/9 | 32 | 2.8 | — |
| | SQX + DMHP | — | 40 | 20 | 9/10 | 19 | 4.0 | — |
| | SQX DV | 20 | 40 | — | 0/10 | 80 | 2.0 | + |
| | SQX DV + DMHP | 20 | 40 | 20 | 0/10 | 90 | 1.2 | ++ |

| Expt. No. | Ratio of SQX/DV | Concn. SQX in diet p.p.m | Concn. DV in diet p.p.m | Concn. DMHP in diet p.p.m | Mortality from Coccidiosis | % Wt Gain | Lesion Score | Activity |
|---|---|---|---|---|---|---|---|---|
| 5 | Uninfected untreated control | | | | 0/20 | 100 | 0.0 | |
| | Infected untreated control | | | | 19/20 | 18 | 3.9 | |
| | 1:1 | 20 | 20 | 40 | 0/20 | 97 | 0.5 | +++ |
| | | 20 | 20 | 20 | 0/20 | 94 | 1.5 | ++ |
| | | 20 | 20 | 10 | 1/20 | 84 | 2.3 | + |
| | | 20 | 20 | 5 | 2/20 | 73 | 2.8 | ± |
| | 2:1 | 26.7 | 13.3 | 40 | 1/20 | 97 | 0.9 | +++ |
| | | 26.7 | 13.3 | 20 | 0/20 | 87 | 1.4 | ++ |
| | | 26.7 | 13.3 | 10 | 3/20 | 69 | 2.8 | ± |
| | | 26.7 | 13.3 | 5 | 8/20 | 87 | 3.2 | — |
| | 3:1 | 30 | 10 | 40 | 0/20 | 92 | 1.6 | ++ |
| | " | 30 | 10 | 20 | 7/72 | 84 | 2.3 | — |
| | " | 30 | 10 | 10 | 7/19 | 60 | 3.2 | — |
| | " | 30 | 10 | 5 | 11/20 | 57 | 3.5 | — |
| | 4:1 | 32 | 8 | 40 | 0/20 | 94 | 1.5 | ++ |
| | " | 32 | 8 | 20 | 3/20 | 83 | 2.7 | ± |
| | " | 32 | 8 | 10 | 9/20 | 71 | 3.2 | — |
| | " | 32 | 8 | 5 | 15/20 | 40 | 3.7 | — |
| | 5:1 | 33.4 | 6.6 | 40 | 1/20 | 100 | 2.0 | + |
| | " | 33.4 | 6.6 | 20 | 7/20 | 70 | 3.4 | — |
| | " | 33.4 | 6.6 | 10 | 12/20 | 42 | 3.6 | — |
| | " | 33.4 | 6.6 | 5 | 18/20 | 31 | 3.9 | — |
| | 1:1 | 20 | 20 | — | 5/20 | 72 | 3.0 | — |
| | 2:1 | 26.7 | 13.3 | — | 16/20 | 77 | 3.8 | — |
| | 3:1 | 30 | 10 | — | 18/20 | 23 | 3.9 | — |
| | 4:1 | 32 | 8 | — | 19/20 | 2 | 4.0 | — |
| | 5:1 | 33.4 | 6.6 | — | 15/20 | 42 | 3.7 | — |
| | | — | — | 40 | 19/20 | 7 | 3.9 | — |
| | | — | — | 20 | 18/20 | 15 | 3.9 | — |
| | | — | — | 10 | 19/20 | 2 | 3.9 | — |
| | | — | — | 5 | 20/20 | — | 4.0 | — |

| Expt. | Treatment | Concn. SQX in diet p.p.m | Concn. DV in diet p.p.m | Concn. DMHP in diet p.p.m | Total Oocysts × $10^6$ Days 5 & 6 | % Wt Gain | Lesion Score | Activity |
|---|---|---|---|---|---|---|---|---|
| 6 | Uninfected untreated control | | | | -ve | 100 | 0.0 | |
| | Infected untreated control | | | | 24.48 | 48 | 3.3 | — |
| | SQX + DV | 30 | 30 | — | -ve | 95 | 0.2 | +++ |
| | SQX + DV + DMHP | 30 | 30 | 250 | -ve | 105 | 0.0 | +++ |
| | SQX + DV + DMHP | 30 | 30 | 90 | -ve | 109 | 0.1 | +++ |
| | SQX + DV + DMHP | 30 | 30 | 30 | -ve | 107 | 0.0 | +++ |
| | SQX + DV + DMHP | 30 | 30 | 10 | -ve | 99 | 0.0 | +++ |
| 7 | Uninfected untreated control | | | | -ve | 100 | | |
| | Infected untreated control | | | | 11.45 | 58 | | |
| | DMHP | — | — | 90 | 5.06 | 108 | | ++ |
| | DMHP | — | — | 30 | 4.57 | 97 | | ++ |
| | DMHP | — | — | 10 | 8.84 | 73 | | + |
| | DMHP | — | — | 5 | 16.18 | 78 | | + |
| | SQX + DV | 10 | 10 | — | 6.42 | 88 | | + |
| | SQX + DV + DMHP | 10 | 10 | 90 | -ve | 115 | | +++ |
| | SQX + DV + DMHP | 10 | 10 | 30 | 1.12 | 110 | | ++ |
| | SQX + DV + DMHP | 10 | 10 | 10 | 2.35 | 98 | | ++ |
| | SQX + DV + DMHP | 10 | 10 | 5 | 5.81 | 103 | | ++ |
| 8 | Uninfected untreated control | | | | 0.0 | 100 | | |
| | Infected untreated control | | | | 0.07 | −2 | | |
| | DMHP | | | 30 | 0.0 | 5 | | — |
| | DMHP | | | 10 | 0.0 | 12 | | — |
| | DMHP | | | 5 | 0.0 | 6 | | — |
| | SQX + DV | 10 | 10 | — | 2.304 | 25 | | — |
| | SQX + DV + DMHP | 10 | 10 | 30 | 0.0 | 79 | | ++ |
| | SQX + DV + DMHP | 10 | 10 | 10 | 0.0 | 83 | | ++ |
| | SQX + DV + DMHP | 10 | 10 | 5 | 1.76 | 70 | | ++ |

TABLE 4-continued

| No. | Treatment | p.p.m | p.p.m | p.p.m | Mortality | Gain | Score | Activity |
|---|---|---|---|---|---|---|---|---|
| 9 | Uninfected untreated control | | | | 0/20 | 100 | 0.0 | |
|  | Infected untreated control | | | | 12/20 | 29 | 3.6 | |
|  | SQX + DV | 80 | 20 | — | 0/20 | 102 | 0.5 | +++ |
|  | " | 60 | 15 | — | 0/20 | 93 | 2.0 | ++ |
|  | " | 40 | 10 | — | 7/20 | 61 | 3.3 | — |
|  | " | 20 | 5 | — | 12/20 | 38 | 3.6 | — |
|  | SQX + DV + DMHP | 80 | 20 | 30 | 0/20 | 105 | 0.0 | +++ |
|  | " | 60 | 15 | 22.5 | 0/20 | 106 | 0.0 | +++ |
|  | " | 40 | 10 | 15 | 0/20 | 82 | 2.1 | + |
|  | " | 20 | 5 | 7.5 | 13/20 | 34 | 3.7 | — |
|  | SQX + DV + DMHP | 80 | 20 | 20 | 0/20 | 104 | 0.0 | +++ |
|  | " | 60 | 15 | 15 | 0/20 | 102 | 0.3 | +++ |
|  | " | 40 | 10 | 10 | 0/20 | 77 | 2.3 | + |
|  | " | 20 | 5 | 5 | 12/20 | 25 | 3.6 | — |
|  | SQX + DV + DMHP | 80 | 20 | 15 | 0/19 | 106 | 0.0 | +++ |
|  | " | 60 | 15 | 11.3 | 0/19 | 102 | 0.5 | +++ |
|  | " | 40 | 10 | 7.5 | 1/20 | 78 | 2.9 | — |
|  | " | 20 | 5 | 3.8 | 8/20 | 55 | 3.3 | — |
|  | SQX + DV + DMHP | 80 | 20 | 10 | 0/20 | 99 | 0.0 | +++ |
|  | " | 60 | 15 | 7.5 | 0/20 | 97 | 1.1 | ++ |
|  | " | 40 | 10 | 5 | 0/20 | 70 | 2.7 | + |
|  | " | 20 | 5 | 2.5 | 11/20 | 29 | 3.6 | — |
|  | SQX + DV + DMHP | 80 | 20 | 5 | 0/20 | 102 | 0.2 | +++ |
|  | " | 60 | 15 | 3.8 | 0/20 | 98 | 1.2 | +++ |
|  | " | 40 | 10 | 2.5 | 3/20 | 72 | 3.0 | — |
|  | " | 20 | 5 | 1.3 | 12/20 | 32 | 3.6 | — |

TABLE 5

| GROUP | 15:85 DV/SQX p.p.m. | DMHP p.p.m. | Cumulative Mortality on days: | | | | | | | | | | Average Weight of chicks, Day of treatment (gm) | Average Weight of surviving chicks (gm) | Weight gain (% of control) |
|---|---|---|---|---|---|---|---|---|---|---|---|---|---|---|---|
| | | | 1 | 2 | 3 | 4 | 5 | 6 | 7 | 8 | 9 | 10 | | | |
| 1 | 50 | 20 | — | — | — | — | 1 | 1 | 1 | 1 | 1 | 1 | 131 | 261.0 | 86 |
| 2 | 50 | 10 | — | — | — | — | — | — | — | — | — | — | 126.5 | 244.0 | 77 |
| 3 | 50 | 5 | — | — | — | — | 1 | 1 | 1 | 1 | 1 | 1 | 130.5 | 202.0 | 47 |
| 4 | 25 | 20 | — | — | 2 | 4 | 5 | 6 | 6 | 6 | 6 | 6 | 127.5 | 225.0 | 64 |
| 5 | 25 | 10 | — | 1 | 2 | 3 | 4 | 5 | 5 | 5 | 5 | 5 | 124.5 | 179.0 | 36 |
| 6 | 25 | 5 | — | 1 | 1 | 3 | 4 | 5 | 6 | 6 | 6 | 6 | 130.5 | 131.0 | — |
| 7 | 100 | — | — | — | — | — | — | — | — | — | — | — | 132.0 | 233.5 | 67 |
| 8 | 50 | — | — | 4 | 4 | 5 | 6 | 7 | 9 | 9 | 9 | 9 | 122.0 | 105.0 | — |
| 9 | 25 | — | — | 3 | 3 | 6 | 8 | 10 | | | | | 129.0 | — | — |
| | DV SQX | | | | | | | | | | | | | | |
| 10 | 30 — | — | — | 2 | 5 | 5 | 6 | 6 | 7 | 7 | 7 | 7 | 131.0 | 140.0 | — |
| 11 | 15 — | — | — | 1 | 2 | 2 | 5 | 8 | 9 | 10 | | | 126.0 | — | — |
| 12 | — 170 | — | — | — | — | — | — | — | — | — | — | — | 133.0 | 259.5 | 84 |
| 13 | — 85 | — | — | — | — | — | 1 | 1 | 1 | 1 | 1 | 1 | 130.0 | 234.0 | 69 |
| 14 | — | — | — | 3 | 3 | 6 | 9 | 9 | 10 | | | | 126.5 | — | — |
| 15 | (uninfected) | — | — | — | — | — | — | — | — | — | — | — | 131.0 | 282.5 | 100 |

TABLE 6

| GROUP | 15:85 TMP SQX p.p.m. | DMHP p.p.m | Cumulative Mortality on days: | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| 1 | 25 | 20 | 0 | 1 | 2 | 2 | 5 | 5 | 6 | 7 | 7 | 7 | 7 |
| 2 | 25 | 10 | 0 | 4 | 4 | 5 | 8 | 8 | 8 | 8 | 8 | 8 | 8 |
| 3 | 25 | 5 | 0 | 4 | 4 | 7 | 9 | 9 | 9 | 9 | 9 | 9 | 9 |
| 4 | 12.5 | 20 | 0 | 2 | 2 | 5 | 7 | 8 | 9 | 9 | 9 | 9 | 9 |
| 5 | 12.5 | 10 | 0 | 3 | 3 | 6 | 10 | | | | | | |
| 6 | 12.5 | 5 | 0 | 4 | 4 | 7 | 10 | | | | | | |
| 7 | 50 | — | 0 | 0 | 0 | 0 | 0 | 0 | 0 | 0 | 0 | 0 | 0 |
| 8 | 25 | — | 0 | 1 | 1 | 5 | 9 | 9 | 10 | | | | |
| 9 | 12.5 | — | 0 | 4 | 6 | 8 | 9 | 9 | 10 | | | | |
| | TMP SQX | | | | | | | | | | | | |
| 10 | 15 — | — | 0 | 4 | 4 | 8 | 10 | | | | | | |
| 11 | 30 — | — | 0 | 2 | 5 | 8 | 8 | 10 | | | | | |
| 12 | — 85 | — | 0 | 0 | 0 | 1 | 1 | 1 | 1 | 1 | 1 | 1 | 1 |
| 13 | — 42.5 | — | 0 | 5 | 6 | 7 | 10 | | | | | | |
| 14 | — — | — | 3 | 3 | 4 | 7 | 9 | 10 | | | | | |

TABLE 7

M.I.C. in μg/ml. and increase in activity of sulphamethoxazole and trimethoprim

| Cmpd | Conc. of DMHP μg/ml. | Sulphamethoxazole M.I.C. | Activity | Trimethoprim M.I.C. | Activity | Trimethoprim in the Presence of × 20 sulphamethoxazol M.I.C. | Activity |
|---|---|---|---|---|---|---|---|
| — | Nil | 1.0 | | 0.3 | | 0.015 | |
| DMHP | 25 | 0.03 | ×100 | 0.0015 | ×300 | <0.00015 | >×300 |
| | 12.5 | 0.3 | ×10 | 0.015 | ×30 | 0.0005 | ×100 |
| | 6.2 | 0.3 | ×10 | 0.015 | ×30 | 0.0015 | ×30 |
| | 3.1 | 1.0 | ×1 | 0.05 | ×10 | 0.005 | ×10 |

TABLE 8

Percentage of inhibition at 7 hrs.

| Drugs - μg/ml. | | DMHP Nil | | DMHP 5 μg/ml. | | DMHP 10 μg/ml. | |
|---|---|---|---|---|---|---|---|
| Trimethoprim | Sulphamethoxazole | Test 1 | Test 2 | Test 1 | Test 2 | Test 1 | Test 2 |
| 0.004 | — | 8 | 6 | 0 | 3 | 85 | 55 |
| 0.002 | — | 10 | 12 | 0 | 1 | 0 | 39 |
| 0.002 | 0.1 | 17 | 1 | 74 | 99 | 97 | 96 |
| 0.002 | 0.2 | 19 | 14 | 95 | 97 | 98 | 99 |
| 0.001 | 0.1 | 0 | 1 | 96 | 98 | 97 | 98 |
| — | 0.1 | 16 | 8 | 20 | 89 | 87 | 97 |
| — | 0.2 | 34 | 10 | 51 | 98 | 94 | 90 |

TABLE 9

Percentage of inoculum viable at 24 hrs.

| Drugs - μg./ml. | | DMHP Nil | | DMHP 5 μg./ml | | DMHP 10 μg./ml | |
|---|---|---|---|---|---|---|---|
| Trimethoprim | Sulphamethoxazole | Test 1 | Test 2 | Test 1 | Test 2 | Test 1 | Test 2 |
| 1.0 | — | >100 | >100 | 41 | — | 15 | 7 |
| 0.3 | — | >100 | >100 | >100 | — | >100 | >100 |
| 0.1 | 1.0 | >100 | 85 | 100 | — | 0.33 | 24 |
| — | 1.0 | >100 | >100 | >100 | — | >100 | >100 |
| — | 3.0 | >100 | >100 | >100 | — | 45 | >100 |
| — | 10.0 | >100 | >100 | 3 | — | 8 | <1 |

TABLE 10

| | Staphylococcus aureus | | | Pseudomonas aeruginosa | | |
|---|---|---|---|---|---|---|
| Drug (μg/ml) | TMP (30) | SMX (300) | TMP + SMX (5) (100) | TMP (30) | SMX (300) | TMP + SMX (5) (100) |
| R = CH₂OH R = R² = Et (30) | 12.5 (17.0) | 12.5 (17.0) | 12.5 (17.0) | Not Tested | | |
| R = CH₂OH R = R² = Et (10) | 10.5 (13.0) | 10.5 (14.0) | 11.0 (14.5) | (5.0) | 13 (16.0) | 8.0 (12.0) |
| R = CH₂OH R = R² = Et (3) | 8.5 (10.5) | 6.5 (12.5) | 10.5 (12.5) | (3.0) | 9.0 (13.0) | 7.0 (10.0) |
| DMHP (30) | 11.0 (14.0) | 9.0 (14.5) | 11.5 (14.5) | Not Tested | | |
| DMHP (10) | 8.5 (10.5) | 5.0 (12.0) | 10.5 (12.0) | (6.0) | 15.0 (20.0) | 12.0 (15.0) |
| DMHP (3) | 8.0 (10.0) | 4.0 (10.0) | 10.0 (12.0) | (5.0) | 9.0 (14.0) | 8.0 (11.0) |
| Control | 6.0 (7.0) | 3.0 (7.0) | 8.5 (10.0) | (5.5) | 6.0 (8.0) | 3.5 (5.0) |

TABLE 11

Size of zone in cm (×6 magnification)

| Organism | TMP* 1.25 μg No DMHP | + DMHP 100 μg | SMX 23.75 μg No DMHP | + DMHP 100 μg | TMP + SMX 1.25 μg 23.75 μg No DMHP | + DMHP 100 μg | DMHP 100 μg |
|---|---|---|---|---|---|---|---|
| Staphylococcus aureus CN 491 | 21 | 24 | 26 | 28 | 34 | 36 | 0 |
| Streptococcus faecalis CN 478 | 28 | 34 | 0 | 14 | 36 | 36 | 10 |
| Escherichia coli CN 314 | 34 | 34 | 28 | 28 | 38 | 38 | 0 |
| Proteus vulgaris CN 329 | 19 | 20 | 36 | 36 | 42 | 42 | 0 |

TABLE 11-continued

| | Size of zone in cm (×6 magnification) | | | | | |
|---|---|---|---|---|---|---|
| | TMP* 1.25 μg | | SMX 23.75 μg | | TMP + SMX 1.25 μg 23.75 μg | |
| Organism | No DMHP | + DMHP 100 μg | No DMHP | + DMHP 100 μg | No DMHP | + DMHP 100 μg | DMHP 100 μg |
| Pseudomonas aeruginosa CN 200 | 0 | 26 | 32 | 36 | 30 | 36 | 22 |

*per 6 mm filter-paper disc

TABLE 12

| TMP mg./mouse | SMX mg./mouse | DMHP mg./mouse P.O. | DMHP mg./mouse I.P. | Average day survival | % survival | Enhancement by DMHP |
|---|---|---|---|---|---|---|
| 2.0 | — | — | — | 6.33 | 0 | / |
| | 2.0 | — | — | 6.80 | 0 | ± |
| | | — | 2.0 | 4.00 | 0 | — |
| 1.0 | — | — | — | 2.0 | 0 | / |
| | 1.0 | — | — | 4.83 | 0 | + |
| | | — | 1.0 | 3.50 | 0 | ± |
| 0.5 | — | 0.5 | — | 1.50 | 0 | — |
| | | — | 0.5 | 3.83 | 0 | + |
| — | 2.0 | — | — | 10.83 | 50 | / |
| | 1.0 | — | — | 10.50 | 50 | / |
| | 0.5 | — | — | 3.66 | 0 | / |
| | | 2.0 | — | 6.83 | 0 | + |
| | | — | 2.0 | 4.60 | 0 | + |
| | 0.25 | 1.0 | — | 5.0 | 0 | + |
| | | — | 1.0 | 4.16 | 0 | + |
| | | 0.5 | — | 1.83 | 0 | ? |
| | | — | 0.5 | 2.16 | 0 | ? |
| 1.0 | 0.25 | — | — | 14 | 100 | / |
| 0.5 | 0.125 | — | — | 12.60 | 66.6 | / |
| | | 0.5 | — | 13.50 | 16.6 | ± |
| | | — | 0.5 | 7.16 | 0 | — |
| | | 2.0 | — | <0.16 | 0 | / |
| | | — | 2.0 | 0.83 | 0 | / |
| | | 1.0 | — | <0.16 | 0 | / |
| | | — | 1.0 | 0.16 | 0 | / |
| | | 0.5 | — | <0.16 | 0 | / |
| | | — | 0.5 | 0.16 | 0 | / |
| — | — | — | — | 0.16 | 0 | / |

TABLE 13

| | | DMHP mg/mouse | | | | | |
|---|---|---|---|---|---|---|---|
| | | Nil | | 2 mg orally | | 2 mg intraperitoneal | |
| Drug mg/mouse | | Average survival | | Average survival | | Average survival | |
| Sulphamethoxazole | Pyrimethamine | time-days | % Survival | time-days | % Survival | time-days | % survival |
| | 0.8 | >15.33 | 33.3 | >17.83 | 50 | 4.0 | 0 |
| | 0.4 | >18.83 | 33.3 | >17.0 | 33.3 | >12.0 | 0 |
| | 0.2 | 10.16 | 0 | 9.16 | 0 | 8.66 | 0 |
| | 0.1 | 8.16 | 0 | 7.83 | 0 | 6.16 | 0 |
| 1 | 0.4 | >19.33 | 16.6 | >24.5 | 66.6 | >21.16 | 50 |
| 1 | 0.2 | >19.33 | 33.3 | >18.5 | 33.3 | >11.16 | 16.6 |
| 1 | 0.1 | 11.0 | 0 | >15.16 | 16.6 | 12.5 | 0 |
| 1 | 0.05 | >12.83 | 16.6 | 10.83 | 0 | 10.16 | 0 |
| Untreated mice | | 6.5 | 0 | 7.0 | 0 | 6.33 | 0 |

EXAMPLE 19

Preparation of 2-amino-7,7-diethyl-7,8-dihydro-4-hydroxy-6-hydroxymethylpteridine (I, $R^1=R^2=$Eth)

Example (i)

Ethyl 3-ethylpent-2-enoate

Sodium hydride (6 g) was placed in a flask with sodium dried benzene (100 ml) and the flask was flushed with oxygen-free dry nitrogen. To this solution was added a slight excess of triethylphosphonoacetate (61.7 g) over a period of 1.5 h and the temperature was maintained at <15° during the addition. The mixture was stirred at this temperature for an additional 1 h and then treated dropwise with pentan-3-one (21.5 g).

After addition of the ketone was complete the reaction mixture was stirred at room temperature until the solid sodium diethyl phosphate had precipitated (approx. 10 h). The mother liquor was decanted from the solid, which was washed with benzene (4×25 ml). The benzene extracts were combined and evaporated in vacuo to give a pale yellow oil (28 g) which was distilled in vacuo to give ethyl 3-ethylpent-2-enoate (21.8 g, yield 56%) as a colourless oil, b.p. 52°–54°/4 mm. Hg.

EXAMPLE (iia)

3-Ethylpent-2-en-1-ol

Ethyl 3-ethylpent-2-enoate (42.3 g) in dry ether (400 ml) was treated dropwise with a 70% solution (in benzene) of a slight excess of sodium dihydro bis ethoxymethoxy aluminate (S.D.A.) (86.1 g), the temperature being maintained at 0° until the addition of the reducing agent was complete. The reaction mixture was then stirred at room temperature for 6 h and the excess S.D.A. was destroyed by the careful addition of water. The solid sodium aluminate which precipitated was filtered off and the filtrate extracted with ethyl acetate (4×50 ml). The combined extracts were washed with brine, dried over sodium sulphate and the solvent removed. The resulting pale yellow oil (23 g) was distilled to give 3-ethylpent-2-en-1-ol (18.5 g, yield 60%) as a colourless viscous oil b.p. 60°/4 mm. Hg.

Example (iib)

3-Ethylpent-2-en-1-ol

A slurry of lithium aluminium hydride (L.A.H.) (8.2 g) in dry ether was added dropwise to a solution of ethyl 3-ethylpent-2-enoate in dry ether (100 ml) at 0°. After the addition of the L.A.H. was complete the mixture was stirred at room temperature for 2 h. The excess L.A.H. was destroyed at 0° by adding a saturated solution of sodium sulphate. The solution was filtered and the filtrate extracted with ethyl acetate and worked up as described in Example 2(a) to give the required alcohol (19 g yield 77%).

Example (iii)

3-Chloro-3-ethyl-2-nitro-pentan-1-ol

Concentrated hydrochloric acid (23 ml) was added dropwise over 1.5 hr. to a mixture of 3-ethylpent-3-en-1-ol (23 g; 0.2 mol.) and amyl nitrite (22.4 g; 0.2 mol.) in glacial acetic acid (46 ml) at 0° (ice-salt bath). After the addition of the acid was complete the mixture was stirred at this temperature for 30 min., then cooled in an acetone-carbon dioxide bath for 15 min. when a white paste formed. The solid was filtered off, washed with water and cold methanol and recrystallised from benzene to give the nitrosochloride (13 g; 36%) as colourless crystals, m.p. 110°.

Example (iv)

3-Amino-3-ethyl-1-hydroxy-pentan-2-one oxime hydrochloride

3-Chloro-3-ethyl-2-nitroso-pentan-1-ol (10 g) was placed in a three-necked round-bottomed flask and treated with a saturated solution of ammonia in methanol. The flask was stoppered, each stopper being secured with copper wire, and the mixture was stirred at room temperature for two days. A clear yellow solution was obtained. The solvent was removed in vacuo at room temperature and the yellow oil obtained was triturated with hot benzene and the benzene decanted. The residue was dissolved in ethanol and the insoluble ammonium chloride present was filtered off. The ethanol was removed in vacuo at room temperature and the residual yellow oil was treated with hot acetone to give a white solid which was filtered off, washed with acetone and recrystallised from butan-2-ol to give the ketoxime hydrochloride (5 g; 46%) as colourless needles, M.Pt. 182°-184°.

Example (v)

2-Amino-4-hydroxy-6-(1,1-diethyl-3-hydroxy-2-hydroxyiminopropylamino)-5-nitropyrimidine A suspension of 2-amino-4-chloro-6-hydroxy-5-nitropyrimidine (2.6 g; 0.0136 mol.) in dry ethanol (50 ml) was treated with 3-amino-3-ethyl-1-hydroxy-pentan-2-one oxime hydrochloride (2.66 g; 0.0136 mol.) and dry triethylamine (2.89 g; 0.0286 mol.) and the mixture was refluxed for 8 hr. The solution was filtered and the filtrate evaporated to dryness in vacuo at room temperature. The yellow oil obtained was treated with cold water and the yellow solid which precipitated was filtered off and washed with water. Recrystallisation from water (charcoal) gave the nitropyrimidine oxime (1.3 g; 30%) as a fine white solid m.p. >250° (decomp.).

Example (vi)

2-Amino-7,7-diethyl-7,8-dihydro-4-hydroxy-6-hydroxymethylpteridine

Sodium dithionite was added portionwise to a warm solution of 2-amino-4-hydroxy-6-(1,1-diethyl-3-hydroxy-2-hydroxyiminopropylamino)-5-nitropyrimidine (450 mg) in 0.1M sodium hydroxide until the colour changed from red to very pale yellow. A solid product was not obtained either on cooling or on adjusting the pH. In order to separate the product from inorganic material the solution was evaporated and the product extracted with ethanol and the inorganic material was filtered off. This extraction was repeated and the combined extracts were evaporated to dryness in vacuo. The residue was dissolved in the minimum quantity of water and placed on a column of Amberlite (C.G.50) ion exchange resin (2.5×28 cm.). Elution with water gave two main fluorescent bands. Evaporation of solution containing the first band gave the 6-carboxaldehyde derivative of the title compound (10 mg., 3%) as a bright orange powder. The second band gave the 7,8-dihydropteridine (160 mg., 44.5%) as a yellow powder.

EXAMPLE 20

Preparation of 2-Amino-7,8-dihydro-4-hydroxy-6-hydroxy-methyl-7-spirocyclohexylpteridine (I, $R^1$, $R^2$=Spirocyclohexyl).

Example (i)

Ethyl cyclo hexylidene acetate

Sodium dried benzene (200 ml) was added to a flask containing sodium hydride (16 g; 0.667 mol.) and the flask was flushed with oxygen-free dry nitrogen. To this mixture was added, over 1 hr., triethylphosphonoacetate (164.3 g; 0.667 mol.+10%) keeping the temperature at 0°. The reaction mixture was stirred for an additional hour at 0° and then treated with cyclohexanone (65.4 g.; 0.667 mol.) at the same temperature. After the addition of the cyclohexanone was complete (~40 min.) the mixture was stirred at room temperature for 3 hr.; stirring became difficult after this time due to a gummy precipitate of sodium diethyl phosphate. The mixture was then heated at 60°-65° for 15 min. during which time it was stirred without difficulty. The mixture was cooled to 15° and the benzene solution was decanted and the solid washed with benzene. The combined mother liquor and washings were evaporated to give a pale yellow oil which on distillation gave the title compound (62 g, 55.4%) as a colourless oil, b.p. 86°-88°/2 mm. Hg

Example (iia)

2-Cyclohexylidene ethanol (1) A 70% solution (in benzene) of sodium dihydrobisethoxymethoxy aluminate (100 g; 0.35 mol.) was added portionwise to ethyl cyclohexylidene acetate (58.8 g; 0.35 mol.) in dry ether (300 ml) at 0°. The reaction mixture was stirred for 6 hr. at room temperature and the excess reducing agent was destroyed by the addition of water. The solid sodium aluminate was filtered off and the filtrate extracted with ethyl acetate (4×50 ml). The combined extracts were washed with brine, dried over sodium sulphate and the solvent evaporated in vacuo. A pale yellow oil was obtained which on distillation gave 2-cyclohexylidene ethanol (31 g, 70%) as a colourless oil, b.p. 80°/2 mm. Hg.

Example (iib)

(2) A solution of ethyl cyclohexylidene acetate (60 g; 0.36 mol.) in dry ether (300 ml.) was cooled to 0° and treated portionwise with a slurry of lithium aluminium hydride (15 g; 0.45 mol.) in dry ether (150 ml), the temperature being kept below 5° during the addition. The reaction mixture was stirred for 15 min. at this temperature and for an additional 20 min. at room temperature. The excess hydride was destroyed with saturated sodium sulphate and the ethereal solution worked up as above to give the alcohol (23 g; 51%) as a colourless oil.

Example (iii)

3-Chloro-2-nitroso-3-spirocyclohexylpropan-1-ol (V)

2-Cyclohexylidene ethanol (23 g; 0.18 mol.) was dissolved in glacial acetic acid (76 ml). Amyl nitrite (21.5 g; 0.18 mol.) was added and the mixture was cooled in an ice-salt bath. The cooled solution was treated dropwise with cold concentrated hydrochloric acid (23 ml) with stirring. After the addition of the acid was complete the reaction mixture was stirred at the same temperature for 30 min., followed by cooling in an acetone-carbon dioxide bath for 10 min. The buff-coloured solid was filtered off, washed with cold methanol and recrystallised from acetone to give the nitrosochloride (15 g., 43%) as colourless needles, m.p. 130°.

Example (iv)

3-Amino-1-hydroxy-3-spirocyclohexylpropan-2-one oxime hydrochloride

A solution of methanol saturated with ammonia was added to 3-chloro-2-nitroso-3-spirocyclohexylpropan-1-ol (14.5 g; 0.075 mol.) in a tightly secured stoppered flask and the mixture was stirred for three days at room temperature. The reaction mixture was then refluxed for 1.5 hr. in an atmosphere of ammonia, cooled and filtered. The solvent was removed and the residual yellow oil washed with hot benzene and decanted. The solid was recrystallised from ethanol giving the oxime hydrochloride (7.8 g, 50%) as colourless crystals, M.Pt. 197°.

Example (v)

2-Amino-4-hydroxy-6-(3-hydroxy-2-hydroxyimino-1-spirocyclohexylpropylamino)-5-nitropyrimidine A suspension of 2-amino-4-chloro-6-hydroxy-5-nitropyrimidine (2.3 g; 0.012 mol.) in dry ethanol was treated with 3-amino-1-hydroxy-3-spirocyclohexylpropan-2-one oxime hydrochloride (2.5; 0.012 mol.) and dry triethylamine (2.7 g; 0.026 mol.) and the mixture was refluxed for 7 hr. The reaction mixture was filtered and the solid washed with hot ethanol. The solvent was removed from the filtrate and the resulting yellow oil was triturated with cold water giving a yellow solid which was crystallised from water.

Example (vi)

2-Amino-7,8-dihydro-4-hydroxy-6-hydroxymethyl-7spirocyclohexlpteridine

2-Amino-4-hydroxy-6-(3-hydroxy-2-hydroxyimino-1-spirocyclohexylpropylamino)-5-nitropyrimidine (500 mg.) was dissolved in the minimum of 0.1M sodium hydroxide by warming on the steam bath. Sodium dithionite was added portionwise until an almost colourless solution was obtained. On cooling the dihydropteridine separated and was filtered off and purified by dissolving in 2M HCl and reprecipitated by the addition of 0.88 ammonia to pH 8. On standing the dihydropteridine (150 mg. 37.2%) was obtained as a pale yellow crystalline solid, m.p. >300 (decomp.).

EXAMPLE 21

2-Amino-4-hydroxy-6-bromomethyl-7,7-dimethyl-7,8-dihydropteridine hydrobromide (I, R=CH$_2$Br)

2-Amino-4-hydroxy-6-methyl-7,7-dimethyl-7,8-dihydropteridine (0.5 g) was dissolved with gentle heating in glacial acetic acid (15 ml) and treated dropwise whilst stirring with bromine (0.125 ml) in glacial acetic acid (6 ml). The resulting solution turned a dark red colour and after 10 minutes a grey-green solid separated. After a further 10 minutes at room temperature this solid was filtered off and washed with ethanol and ether to give 0.7 g of product. The title compound (70% yield) was separated from small amounts of the starting material and the dibromomethyl derivative by thin layer chromatography.

EXAMPLE 22

2-Amino-4-hydroxy-6-dibromomethyl-7,7-dimethyl-7,8-dihydropteridine hydrobromide (I, R=CHBr$_2$)

2-Amino-4-hydroxy-6-methyl-7,7-dimethyl-7,8-dihydropteridine (1 g) was dissolved with gentle heating in glacial acetic acid (17 ml) and treated dropwise whilst stirring with bromine (0.5 ml) in glacial acetic acid (7 ml). The reaction mixture was stirred for a further 2 hours, during which time the colour had darkened considerably and a black-green tar had formed. The supernatant solvent was decanted and the tar treated with acetone (20 ml). Trituration followed by filtration gave a dark-green solid (1.5 g). The title compound (86% yield) was separated from small amounts of the starting material and the monobromomethyl derivative by thin layer chromatography.

EXAMPLE 23

Preparation of 2-amino-7,7-dimethyl-7,8-dihydro-4-hydroxy-6-phenoxymethylpteridine (I, R=CH$_2$OPh)

3,3-dimethylallylphenyl ether was prepared from 3,3-dimethylacrylic acid by reduction with sodium dihydro-bis (2-methoxyethoxy) aluminate in benzene, chlorination of the resulting 3,3-dimethylallyl alcohol with thionyl chloride and reaction of the product with sodium phenoxide in the presence of a polar solvent.

Following the procedure disclosed in the specification of German Offenlegungschrift No. 2,137,339, the 3,3-dimethylallylphenyl ether thereby obtained was then caused to undergo an addition reaction with nitrosyl chloride and the resulting nitrosochloride converted to the corresponding oxime by reaction with ammonia solution. Reacting the oxime with 2-amino-4-chloro-6-hydroxy-5-nitropyrimidine in the presence of triethylamine provided the pyrimidine ketoxime which was then reductively cyclised with sodium dithionite to give 2-amino-7,7-dimethyl-7,8-dihydro-4-hydroxy-6-phenoxymethylpteridine (M.Pt. >300°).

What we claim is:

1. The method of treating a host suffering from a protozoa infection which comprises administering to said host an effective anti-protozoa treatment amount of the combination of a dihydrofolic reductase inhibitor and an effective potentiation amount of a potentiator of said inhibitor which itself also inhibits the enzyme hydroxymethyldihydropteridine pyrophosphokinase, said combination containing 1 to 30 parts of the potentiator and one part of an inhibitor or an equivalent amount of salt thereof.

2. The method of claim 1 in which the potentiator is 2-amino-4-hydroxy-6-hydroxymethyl-7,7-dimethyl-7,8-dihydropteridine.

3. The method of claim 2 in which the protozoa caused infection is coccidiosis.

4. The method of treating a host suffering from a protozoa infection which comprises administering to said host an effective antiprotozoa treatment amount of the combination of a dihydrofolic reductase inhibitor and an effective potentiation amount of a potentiator of said inhibitor which itself also inhibits the enzyme hydroxymethyldihydropteridine pyrophosphokinase, said combination containing 1 to 30 parts of the potentiator and part of an inhibitor or an equivalent amount of a salt thereof, in the above the inhibitor is trimethoprim and the potentiator is 2-amino-4-hydroxy-6-hydroxymethyl-7,7-dimethyl-7,8-dihydropteridine.

* * * * *